April 20, 1965 J. R. BORGHELLO ET AL Plant Pat. 2,497
PEACH TREE
Filed Jan. 31, 1964
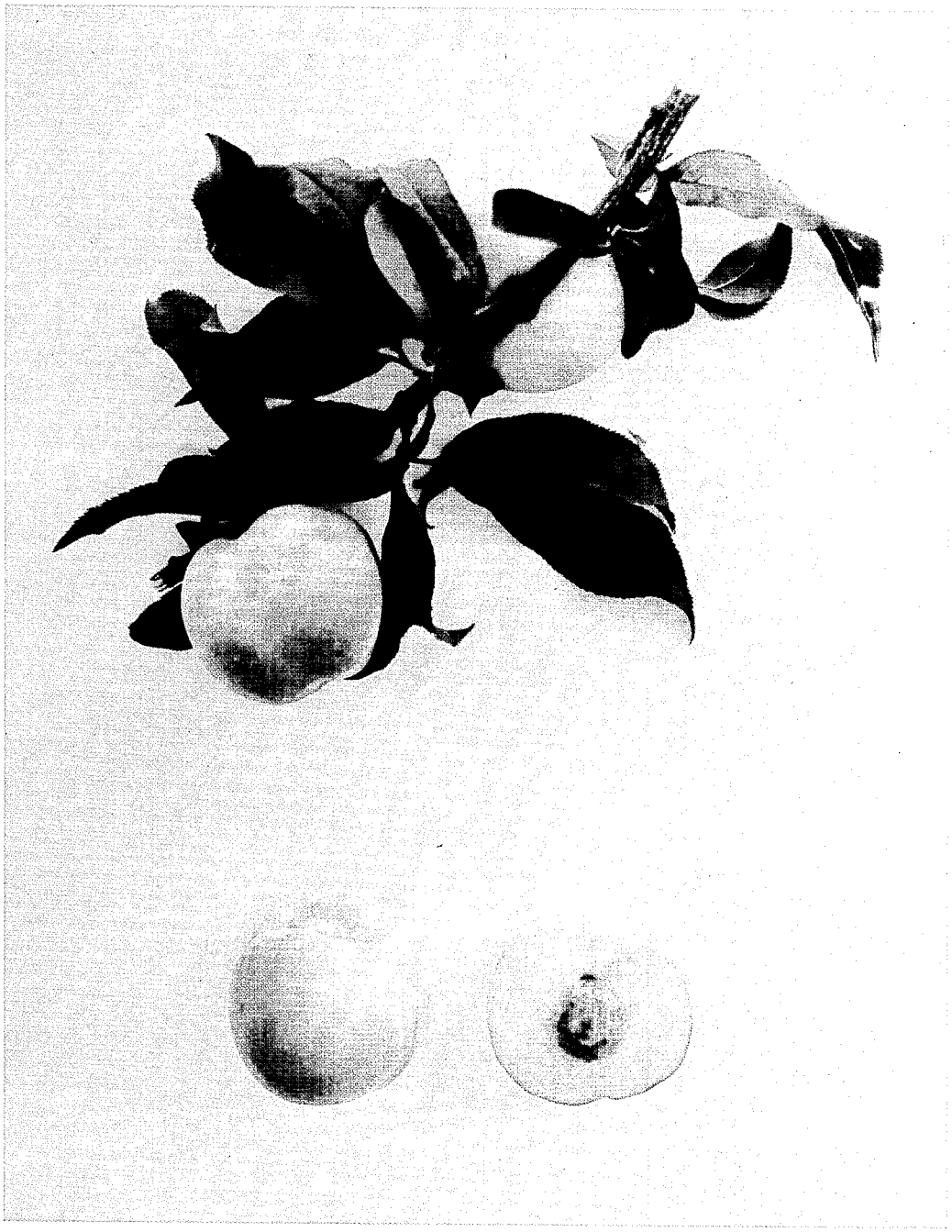
INVENTORS
John R. Borghello
Angelo Ertassi
Webster & Webster
ATTYS.

United States Patent Office

Plant Pat. 2,497
Patented Apr. 20, 1965

2,497
PEACH TREE

John R. Borghello, 415 N. Olive Ave., and Angelo Ertassi, 1232 Brady Ave., both of Modesto, Calif.

Filed Jan. 31, 1964, Ser. No. 341,819
1 Claim. (Cl. Plt.—43)

This discovery relates to a new and distinctive variety of peach tree which bears large, clingstone fruit having yellow flesh, and yellow skin partially overspread with red.

The present variety of peach tree is distinctively characterized, in comparison to other peach varieties in the same area and under like growing conditions, in the following respects:

On the average, the fruit ripens and is in harvest immediately following the Paloro and two or three days ahead of the Gaume; this being of substantial commercial advantage in that a desirable picking sequence is established.

Further, in each year and without exception, the variety has set an extremely heavy crop; the fruit sizing very well, being consistently large, and without the split pits common to other peach varieties that produce large fruit.

The present variety of peach tree was discovered by us growing as a chance seedling in a Halford orchard on our ranch located near Hughson, in the county of Stanislaus, State of California.

Upon such discovery of the variety and recognition by us of the hereinbefore described novel features thereof, the variety was asexually reproduced by budding; this having been undertaken for our account and under our control and direction by a commercial nursery located near Modesto, county of Stanislaus, State of California. Such asexual reproductions were subsequently planted by us on our ranch located as aforesaid. In maturity, such asexual reproductions of the variety ran true to the parent in all respects.

The drawing comprises an illustration, by photographic reproduction in color, of a twig with fruit and leaves; a whole fruit; and a fruit cut in half to expose the flesh, and with the stone remaining in place.

Referring now more specifically to the promological details of this new and distinct variety of peach tree, the following is an outline description thereof; all major color plate identifications, by comparison with fresh specimens, being by reference to Maerz and Paul Dictionary of Color, except where common terms of color definition are employed.

Tree:
- *Size.*—Medium.
- *Vigor.*—Medium to vigorous.
- *Growth.*—Upright.
- *Density.*—Medium.
- *Form.*—Vase-shaped under normal pruning.
- *Hardiness.*—Hardy.
- *Production.*—Very productive.
- *Bearing,*—Regular heavy bearer.

Trunk: Form—medium-stocky.

Branches:
- *Size.*—Medium.
- *Texture.*—Medium-shaggy.
- *Color.*—Brown to reddish brown.

Leaves:
- *Size.* — Large. Average length — 6½". Average width—1¼" to 1¾".
- *Form.*—Lanceolate; acutely pointed.
- *Thickness.*—Medium.
- *Color.*—Top side—medium dark green (23–J–10). Under side—lighter green (23–I–6).
- *Texture.*—Smooth.

- *Petiole.*—Medium length; medium thickness.
- *Glands.*—Eglandular.
- *Margin.*—Serrated.

Flower buds:
- *Hardiness.*—Hardy.
- *Size.*—Small.
- *Length.*—Medium.
- *Form.*—Plump; rounded; free.
- *Pubescence.*—Some pubescence.

Flowers:
- *Blooming period.*—Mid-season, about three days before Halford.
- *Size.*—Small.
- *Color.*—Pink, with high pigmentation in the calyx cup.

Fruit:
- *Maturity when described.*—Hard ripe.
- *Date of picking.*—August 12, 1963, in one picking.
- *Size.*—Large. Average diameter axially—2½" to 3". Average transversely in suture plane—2½" to 3".
- *Form.*—Uniform; globose.
- *Suture.*—Relatively inconspicuous.
- *Ventral surface.*—Lips equal to unequal.
- *Cavity.*—Flaring. Average depth — ⅜". Average breadth—1".
- *Base.*—Rounded.
- *Apex.*—Short; slightly flattened.
- *Pistil point.*—Small.

Skin:
- *Thickness.*—Medium.
- *Texture.*—Medium tough.
- *Tenacity.*—Tenacious.
- *Tendency to crack.*—None.
- *Down.*—Moderate; medium length.
- *Color.*—Yellow (9–L–4) to (10–L–5), partially overspread with red (6–L–4), lightly streaked and mottled with somewhat darker red (7–L–6) .

Flesh:
- *Amygdalin.*—None.
- *Juice.*—Moderate.
- *Texture.*—Firm; crisp.
- *Fibers.*—Fine; tender; light orange.
- *Flavor.*—Mild.
- *Aroma.*—Slight.
- *Eating quality.*—Good.
- *Color.*—Yellow (9–L–4), even from skin to pit cavity.

Stone:
- *Type.*—Cling; adheres to flesh over entire surface.
- *Fibers.*—Short.
- *Size.* — Small. Average length — 1". Average breadth—¾".
- *Form.*—Elliptical.
- *Base.*—Straight.
- *Hilum.*—Oval.
- *Apex.*—Acuminate.
- *Sides.*—Equal.
- *Surface.*—Furrowed; Grooved and pitted.
- *Ridges.*—Rounded.
- *Pits.*—Elongated.
- *Ventral edge.*—Without wing.
- *Dorsal edge.*—Narrow.
- *Tendency to split.*—None.
- *Color.*—Rustic brown (7–H–11).

Use: Culinary; canning; long distance shipping.

Keeping quality: Good.

Shipping Quality: Good.

All of the herein identified previously known and existing varieties of peach trees are unpatented.

The tree and its fruit herein described may vary in slight detail due to climatic and soil conditions under which the variety may be grown; the present description being of the variety as grown in the Central Valley of California.

The following is claimed:

A new and distinct variety of peach tree, substantially as illustrated and described, which is a very productive and regular bearer of large, globose, clingstone fruit having yellow flesh, and yellow skin partially overspread with red; characterized by the fruit being in harvest immediately following the Paloro and two or three days ahead of the Gaume, and by fruit that sizes well, is consistently large, and without split pits.

No references cited.

ABRAHAM G. STONE, *Primary Examiner.*